(12) United States Patent (10) Patent No.: US 8,821,420 B1
Callahan (45) Date of Patent: Sep. 2, 2014

(54) HAND AND WRIST RESTORER

(76) Inventor: Dennis J. Callahan, Maryland Heights, MO (US)

( * ) Notice: Subject to any disclaimer, the term of this patent is extended or adjusted under 35 U.S.C. 154(b) by 772 days.

(21) Appl. No.: 13/012,646

(22) Filed: Jan. 24, 2011

Related U.S. Application Data

(60) Provisional application No. 61/299,241, filed on Jan. 28, 2010.

(51) Int. Cl.
*A61H 1/00* (2006.01)

(52) U.S. Cl.
USPC ............... 601/33; 601/23; 601/136; 601/151; 128/898

(58) Field of Classification Search
CPC ......... A61H 1/00; A61H 1/006; A61H 1/008; A61H 1/02; A61H 1/0237; A61H 1/0274; A61H 2001/00; A61H 2001/02; A61H 2001/0206; A61H 2001/0237; A61H 2009/00; A61H 2201/0157; A61H 2201/1635; A61H 2201/1638; A61H 2201/1645; A61H 2005/06; A61H 2005/10
USPC ........ 601/5, 6, 9, 11, 23, 33, 136, 151; 602/5, 602/16, 20, 21, 23, 26, 13; 482/44, 45, 46; 606/201, 202, 203; 128/898

See application file for complete search history.

(56) References Cited

U.S. PATENT DOCUMENTS

| | | | |
|---|---|---|---|
| 3,415,244 | A | 12/1968 | Block |
| 4,343,302 | A * | 8/1982 | Dillon ........................... 601/152 |
| 5,279,574 | A | 1/1994 | Forren |
| 5,713,818 | A | 2/1998 | Buitoni |
| 6,283,126 | B1 | 9/2001 | Jessen |
| 6,569,066 | B1 | 5/2003 | Patterson et al. |
| 6,681,772 | B2 | 1/2004 | Atwater et al. |
| 7,241,251 | B2 | 7/2007 | Patterson |
| 7,604,582 | B2 | 10/2009 | Abdallah |
| 2003/0056793 | A1 | 3/2003 | Atwater et al. |
| 2003/0105416 | A1* | 6/2003 | Hepburn et al. ................ 601/33 |
| 2004/0215111 | A1* | 10/2004 | Bonutti et al. ..................... 601/5 |
| 2006/0211545 | A1 | 9/2006 | Smyer |
| 2009/0099488 | A1* | 4/2009 | Hedberg ........................... 601/5 |
| 2009/0149305 | A1 | 6/2009 | Abdallah |

* cited by examiner

*Primary Examiner* — Quang D Thanh
(74) *Attorney, Agent, or Firm* — Kevin L. Klug

(57) ABSTRACT

A hand and wrist restorer and method of use having a cuff which is capable of grasping a portion of the outer skin of a limb and securing the fascia tissue thereunder together with a support which allows a user to provide a distal force upon the limb while rotating or moving the distal portion of the limb whereby a stretch of the fascia tissue occurs.

7 Claims, 17 Drawing Sheets

HAND AND WRIST RESTORER

This application claims priority of U.S. Provisional Patent Application No. 61/299,241, filed Jan. 28, 2010, entitled Hand and Wrist Restorer.

BACKGROUND OF THE INVENTION

The art of the present invention relates to in general arm, wrist, and finger dexterity restorative devices and methods of use and more particularly to an apparatus and method of use which promotes a myofascial release by gripping and stretching the fascia tissue within the arm and wrist or other limbs of the body. The apparatus and method of use is usable by patients suffering from a plurality of ailments including those related to sports injuries, arthritis, carpel tunnel syndrome, and repetitive injuries such as those suffered by musicians, athletes, and typists. Myofascial release is a form of soft tissue therapy used to treat somatic dysfunction and accompanying pain and restriction of motion.

Fascia is the soft tissue component of the connective tissue that provides support and protection for most structures within the human body, including muscle. This soft tissue can become restricted due to psychogenic disease, overuse, trauma, infectious agents, or inactivity, often resulting in pain, muscle tension, and corresponding diminished blood flow. Although fascia and its corresponding muscle are the main targets of myofascial release, other tissue may be affected as well, including other connective tissue.

Irritation of fascia or muscle can cause local inflammation. Chronic inflammation results in fibrosis, or thickening of the connective tissue, and this thickening causes pain and irritation, resulting in reflexive muscle tension that causes more inflammation. In this way, the cycle creates a positive feedback loop and can result in ischemia and somatic dysfunction even in the absence of the original offending agent. Myofascial techniques aim to break this cycle through a variety of methods acting on multiple stages of the cycle.

Prior art methods of treatment utilizing myofascial release concepts (i.e. deep tissue work) has practitioners utilizing hands, knuckles, elbows, forearms, or other manual techniques to slowly stretch the restricted fascia by applying a force to the affected area and stretching or elongating the fascia or further mobilizing adhesive tissues. The prior art technique has a practitioner 1.) contacting the surface of the body with the hands, knuckles, elbows, or forearms, 2.) engaging into the soft tissue, 3.) contacting the first barrier or restricted layer, 4.) delineating of a line of tension, 5.) engaging the fascia by taking up the slack in the tissue, and 6.) finally, moving or dragging the fascia across the surface while staying in touch with the underlying layers. Obviously, the effectiveness of this prior art manual technique is highly practitioner dependent and often has limited repeatability.

The present art apparatus and method of use reduces mechanical and repetitive stress on the hands, wrist, and fingers by utilizing deep tissue massage therapy which is rooted in myofascial release concepts and which is highly repeatable. It is understood within the medical arts that throughout the human body is fascia tissue. Fascia tissue generally comprises a sheet or band of fibrous connective tissue enveloping, separating, or binding together muscles, organs, and other soft structures of the body. Fascia tissue can be as restrictive as muscle or scar tissue and may also cause undesired joint surface wear and arthritic conditions if not released.

Release of the binding nature of fascia tissue is generally accomplished by applying a gripping or static pressure technique with a shearing force thereafter applied to the fibers of the fascia tissue. This shearing force stretches the fascia tissue and creates a slight burning sensation when properly performed. The present art apparatus and method of use engages and stretches the fascial glove tissue which surrounds the wrist, hand, and fingers to achieve a myofascial release.

The present art apparatus first comprises a cuff which is able to apply a gripping or static pressure to a limb. That is, the cuff is capable of applying a mild to moderate compression around the wrist or forearm via an at least partially high coefficient of friction (i.e. tacky) surface which is capable of gripping the skin and fascia. In a preferred embodiment, the cuff provides a tacky or rubberized inner lining surface or interface with and substantially around the limb and is able grip the skin and thereby the fascia. Alternate embodiments provide an inflatable cuff or pneumatic bladder (such as or having a similarity to that utilized with a blood pressure monitor) in order to provide a further gripping force. For the preferred embodiment, the cuff also has an adjustable buckle or strap portion which secures the apparatus to the limb of choice with an adequate compression to engage the fascia.

Laterally or distally extending and attached with the cuff is a support structure in the form of one or more winged supports or a cone like structure. The support structure allows the patient or user to touch the apparatus with a structure or surface and thereafter apply a pushing or distally extending force with the limb upon which the apparatus is placed. That is, when the cuff is secured with the skin/fascia, the user applies a distal or downward force to actively engage the skin/fascia glove, preferably while making a first and rotating said fist, whereby a burning sensation is imparted to the fascia while the entire wrist, hand, and fingers are stretched. As stated, the cuff substantially holds the fascia tissue where placed. That is, the cuff holds so tight that the tissue between the cuff and elbow does not substantially move, thereby providing the stretch to the distal forearm fascia and muscular system. This distal force along with any rotation imparted by the user to the distal extremities thereby creates a shearing and/or stretching force on the fascia tissue between the cuff and the end of the extremity upon which the apparatus is mounted. This precisely placed force decompresses the joint lines of the fascia tissue affected. If mounted upon the forearm, this includes the wrist, hand, and finger fascia tissue.

When the aforesaid fascia tissue is decompressed, the patient generally finds a restoration of a range of motion, a greater dexterity, an improvement of fine motor skills, and an overall performance enhancement of the limb and extensions with which the apparatus is utilized.

Prior art hand or wrist therapeutic devices such as found in U.S. Pat. No. 6,569,066 issued to Patterson, et al. rely upon fixed weights or a hand gripping to provide a proprioception improvement without providing any apparatus, method, or disclosure for gripping and stretching the fascia tissue. Although numerous hand and arm protective devices have been found within the medical arts such as U.S. Pat. No. 6,681,772 issued to Atwater, et al., U.S. Pat. No. 6,283,126 issued to Jessen, U.S. Pat. No. 5,279,574 issued to Forren, and U.S. Pat. No. 3,415,244 issued to Block, they have been utilized for protection of the extremities or as a surgical aid and are silent about gripping and/or stretching the fascia.

Unlike the prior art, the present art is capable of holding and engaging the fascia while further allowing the user to rotate his or her wrist (or other extremities) to stretch the fibrous fascia material. The benefits of the present art apparatus and method of use are numerous, including but not limited to, an increased or improved range of motion, dexterity, fine motor skills, and wrist/hand function. The resulting benefits allow increased performance in work, sports, and hobbies, especially when the user is afflicted with carpel tunnel syndrome, arthritis, and/or scar tissue disability. Unlike the prior art, the present art is capable of minimizing extremity numbness, tingling, pain, and poor circulation effects (i.e. cold hands).

Accordingly, it is an object of the present invention to provide a hand and wrist restorer apparatus and method of use which is capable of simultaneously gripping the fascia of a human's extremity while allowing the user to rotate his or her hand and/or wrist and stretch said fascia.

Another object of the present invention is to provide a hand and wrist restorer apparatus and method of use which is able to allow the user to easily provide the aforesaid benefits outside of a medical facility.

Another object of the present invention is to provide a hand and wrist restorer apparatus and method of use which achieves all of the aforesaid benefits in a repeatable fashion via a user supplied distal or downward force upon the user's own extremity.

SUMMARY OF THE INVENTION

To accomplish the foregoing and other objects of this invention there is provided a hand and wrist restorer apparatus and method of use. The apparatus and method of use allows a user to engage and stretch the fascial glove surrounding the wrist, hand, and fingers via a radial and/or ulnar deviation (i.e. flexion and extension) of the hand, wrist and/or fingers while a cuff having a gripping or tacky surface (i.e. somewhat high coefficient of static friction) applies mild to moderate compression around the skin and fascia. The apparatus and method of use is especially useful to persons suffering from blood circulation issues, neurological issues, numbness, tingling, pain, carpel tunnel syndrome, arthritis, and scar tissue complexities. The apparatus and method of use is also useful to promote a decompression of the joint capsules, i.e. decompression of the joints and joint muscles of the knuckles, fingers, wrists, and thumbs.

For the preferred embodiment, the apparatus comprises a cuff and one or more (preferably two) winged supports attached with said cuff. Preferably, said winged supports extend laterally from said cuff and have an at least partially arcuate shape. The cuff has a cylindrical form and is preferably manufactured of a rigid material such as a molded or formed plastic but may be manufactured from a plurality of materials including but not limited to metals and alloys thereof, woods, ceramics, or composites.

For the preferred embodiment, the cuff has a hinged portion, an inner liner or lining, and a buckle or retainer to maintain the cuff in a closed form. The inner liner or lining is preferably of a tacky rubberized material that allows a substantial grip with the limb in wet or dry conditions. This includes materials of a natural or synthetic rubber material, vulcanized rubber, polyurethane open or closed cell foam, or a plurality of natural or synthetic materials which provide a slight cushioning and frictional grip with the limb. An especially useful inner liner or lining material is the Gelsmart® line of materials from Poly-Gel LLC of Whippany, N.J., including but not limited to the S-GEL (medical-grade silicone), M-GEL (medical-grade mineral oil gel) or the T-GEL (non-mineral-oil elastomeric). Further alternative embodiments utilize a pneumatic or hydraulic bladder in place of said inner liner, with or without the hinged portion. The buckle or retainer is mounted with one of the halves of the cylinder and is retained by the other half via a retainer when the two halves are closed to form the cylindrical shape.

For the preferred embodiment, said winged supports have a shape which allows a patient to support the apparatus upon his or her thighs during use. That is, the user must be able to exert a forward or distal force and a lateral or rotational movement with a portion of the limb extending from the apparatus and upon which the apparatus is mounted.

An alternative embodiment attaches a strap and/or handle with the cuff and allows a user to hold the strap or handle with a single hand while imparting the distal or lateral forces to a particular limb portion. The handle or strap may be secured to the cuff or to the winged supports or to a combination of both.

A further alternative embodiment utilizes a distal cone, conical, semi-conical, partial conical, or frustum shaped form in place of said winged supports. The alternative conical form attaches with the cuff and allows a patient or user to easily apply the forward force onto a surface such as a counter top, wall, or floor.

In operation, the patient or user first places a portion of a limb requiring treatment (usually the forearm) into the open cuff and closes the cuff. The cuff is compressed tightly around the limb and the buckle or retainer is secured with the retainers on the cuff or the pneumatic or hydraulic bladder is inflated or pressurized. The patient or user then places the winged supports onto the thighs, against a surface, or in the case of the partially conical form against a surface such as a table, wall, counter top, or floor. If the strap and/or handle is utilized, the user will hold the handle or strap with a hand prior to therapy. For use with the arm, therapy thereafter begins with the user preferably forming a fist-like form with the hand on the arm upon which the apparatus is mounted in order to maximize the fascia stretch, especially at the back of the hand and knuckle areas. The patient or user then rotates the wrist (either clockwise or counterclockwise). The patient or user holds the first at a particular location which feels the most stretch until the stretch feeling dissipates. When the apparatus is removed, the patient or user will have a looser feeling or more nimble hand, wrist, and fingers. The fascia and scar tissue fibers will be stretched and not constrict the muscle movement as was experienced prior to operation of the apparatus.

The art of the present invention may be manufactured from a plurality of materials including but not limited to metals and alloys thereof, plastics, woods, composites, or ceramics without departing from the scope and spirit herein intended. The apparatus may further be manufactured via molding, machining, casting, forging, pressing, laminating, carving, extruding, or utilization of stereo-lithographic or electro-dynamic milling or other techniques which are appropriate for the material utilized. For the preferred embodiment, the cuff and winged supports or cone is molded from a polyvinylchloride material or spun (conical form) from an aluminum material.

BRIEF DESCRIPTION OF THE DRAWINGS

Numerous other objects, features and advantages of the invention should now become apparent upon a reading of the following detailed description taken in conjunction with the accompanying drawings, in which.

DETAILED DESCRIPTION

Figure 1:
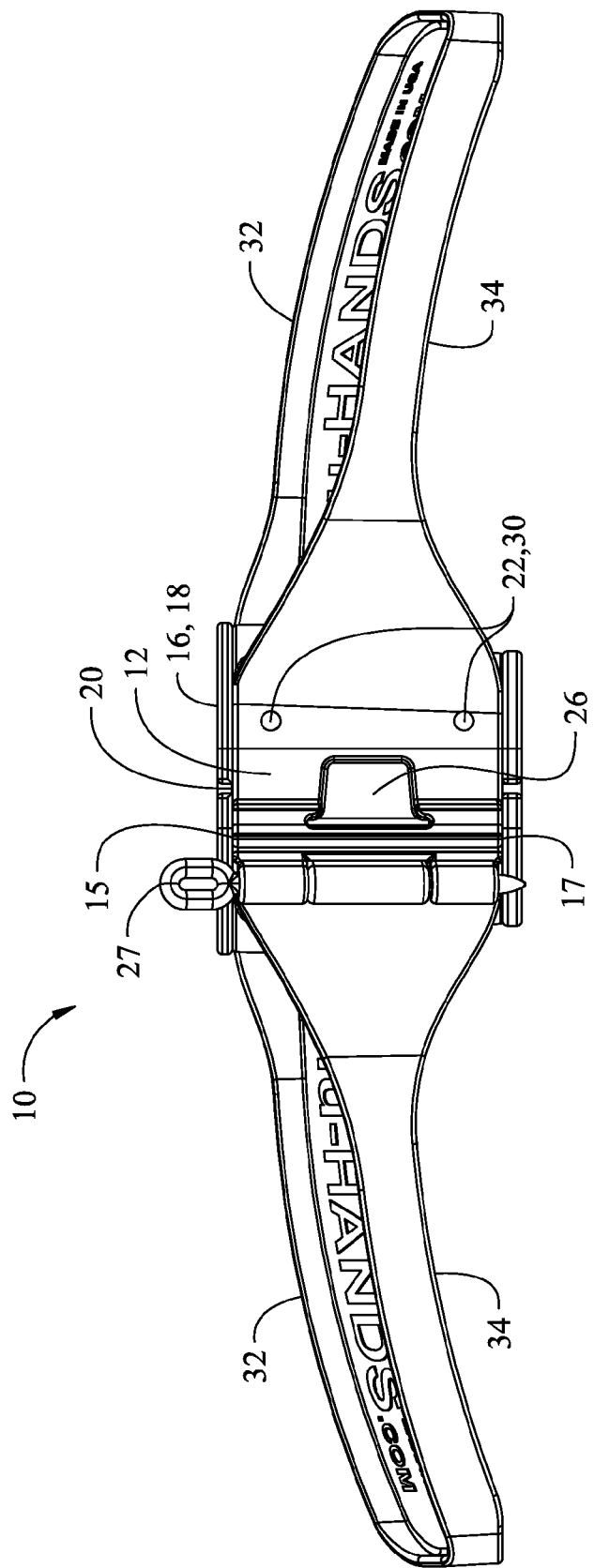
FIG. 1 is a front plan view of a preferred embodiment of a hand and wrist restorer.
Figure 2:
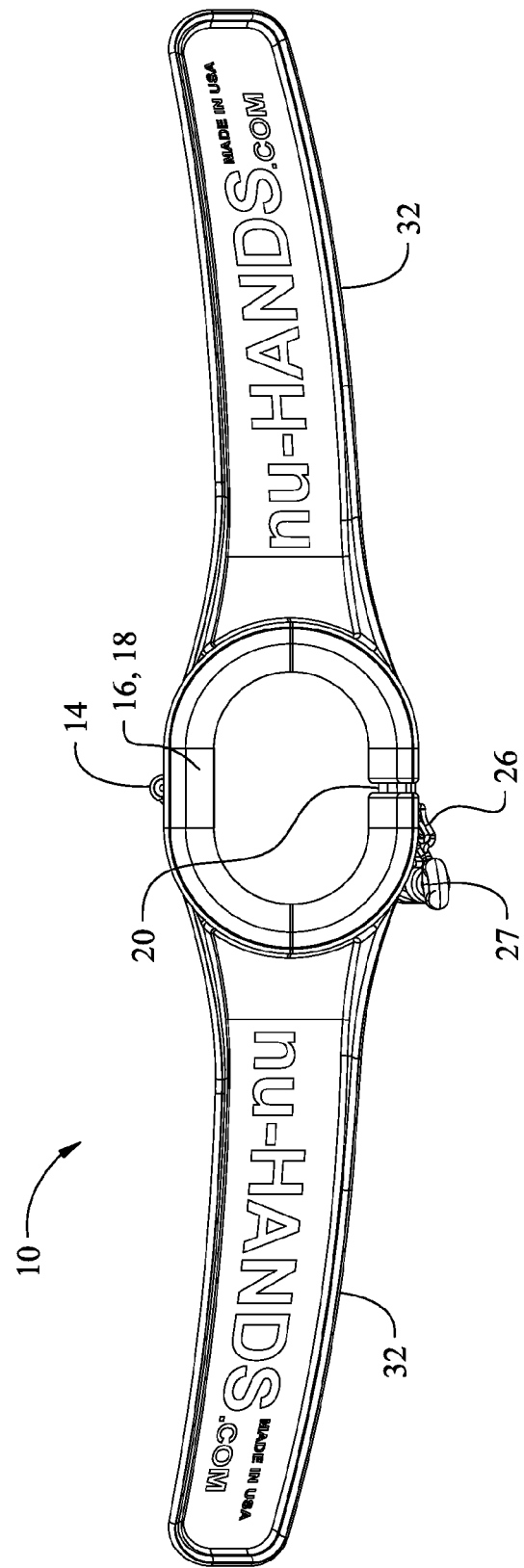
FIG. 2 is a top plan view thereof.
Figure 3:
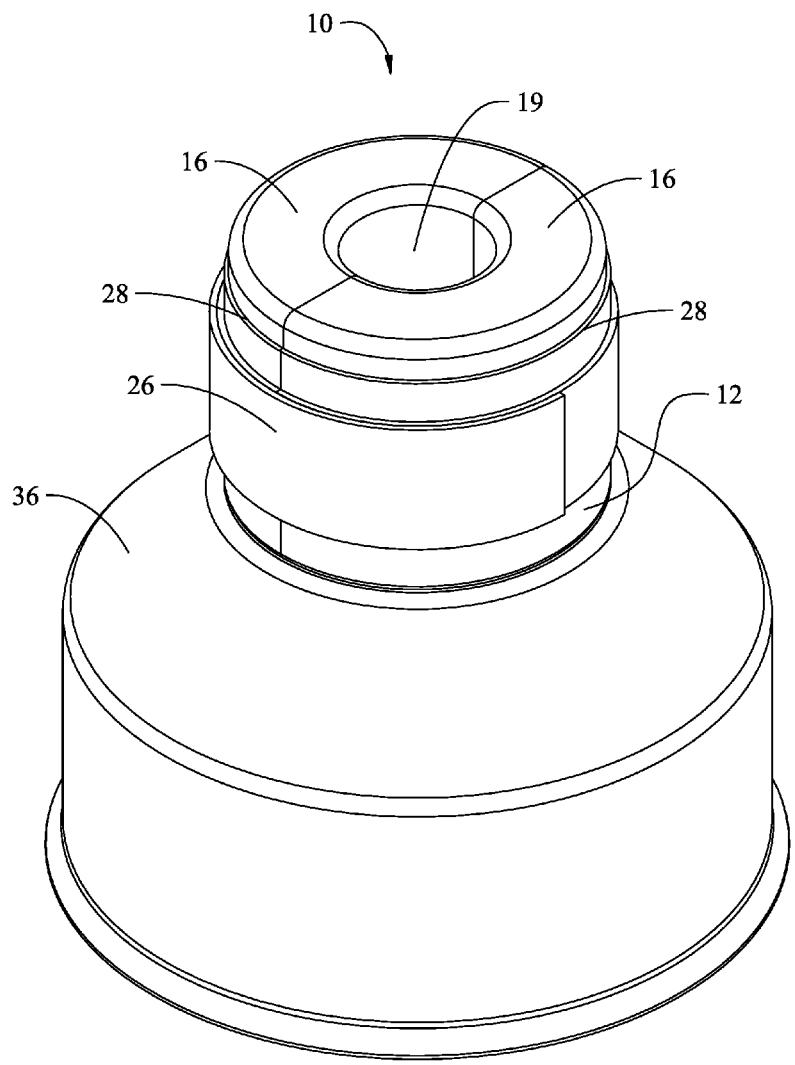
FIG. 3 is a front perspective view of an alternative embodiment of a hand and wrist restorer.
Figure 4:
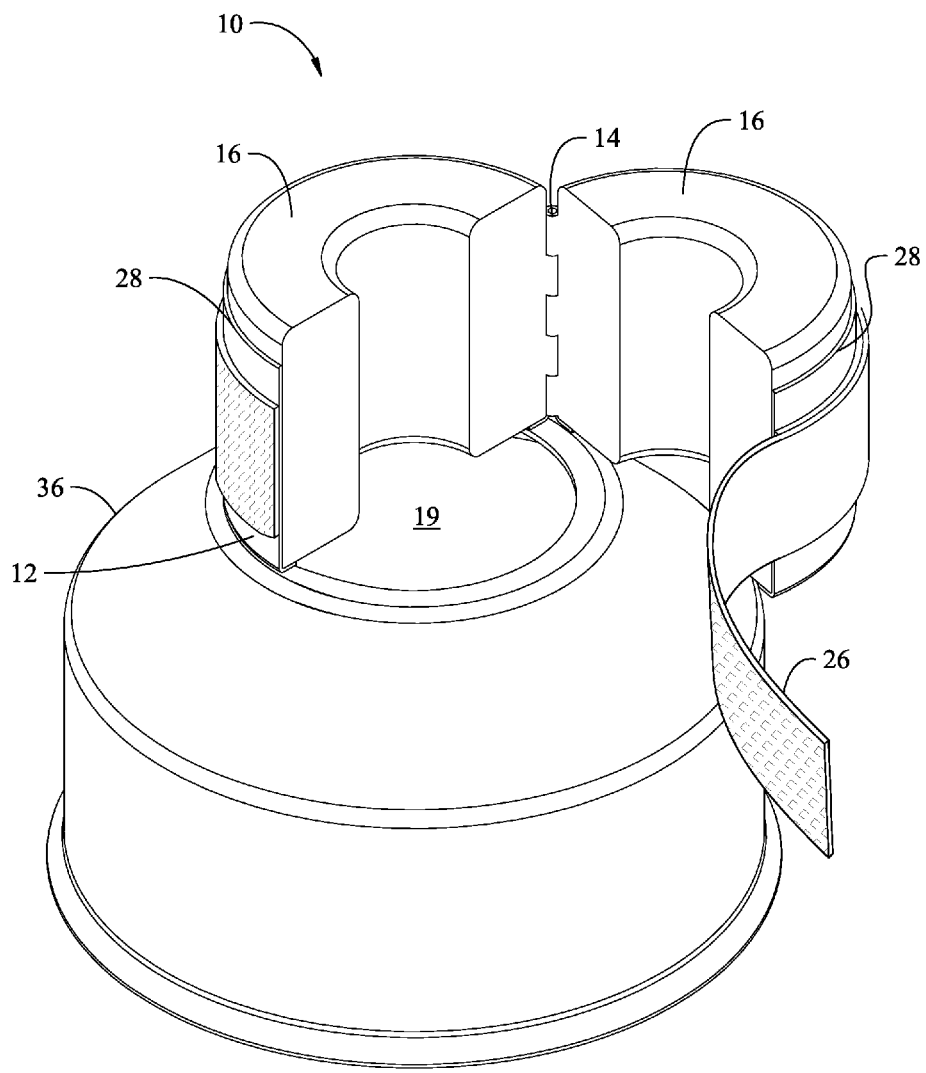
FIG. 4 is a front perspective view of an alternative embodiment of a hand and wrist restorer showing the cuff in an open position.
Figure 5:
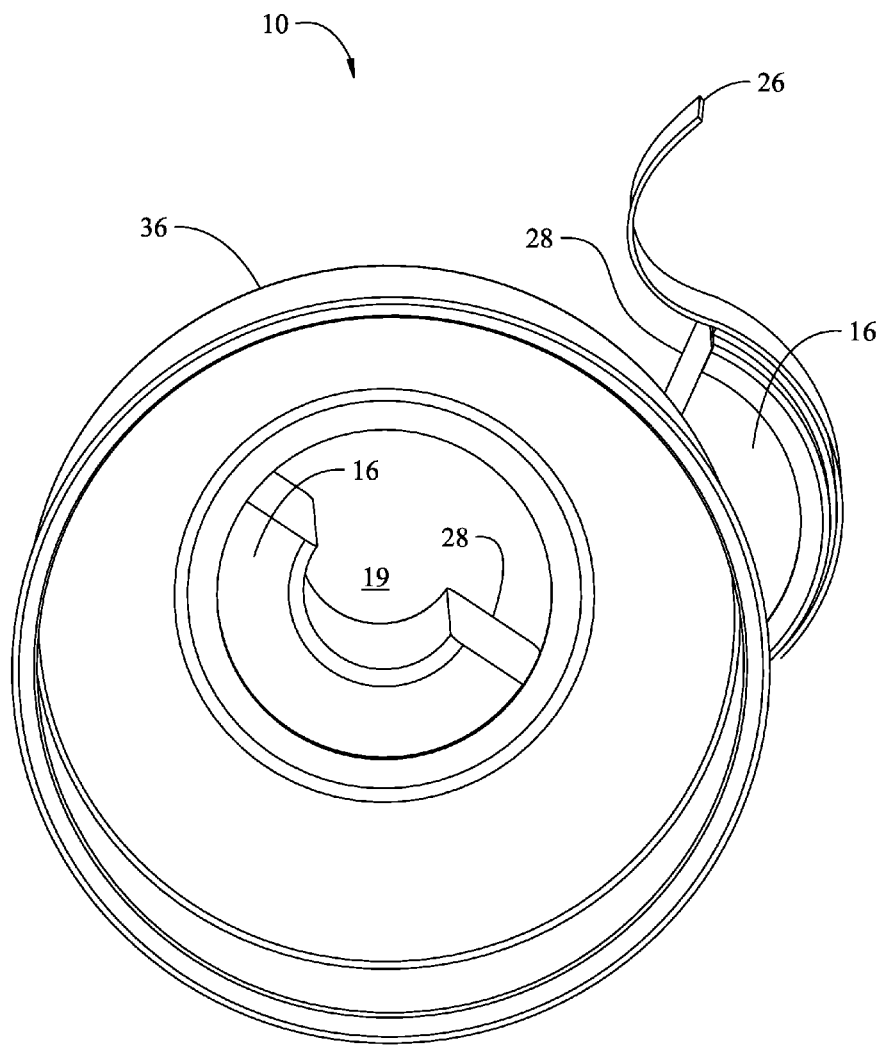
FIG. 5 is a bottom perspective view of an alternative embodiment of a hand and wrist restorer with the cuff in an open position.
Figure 6:
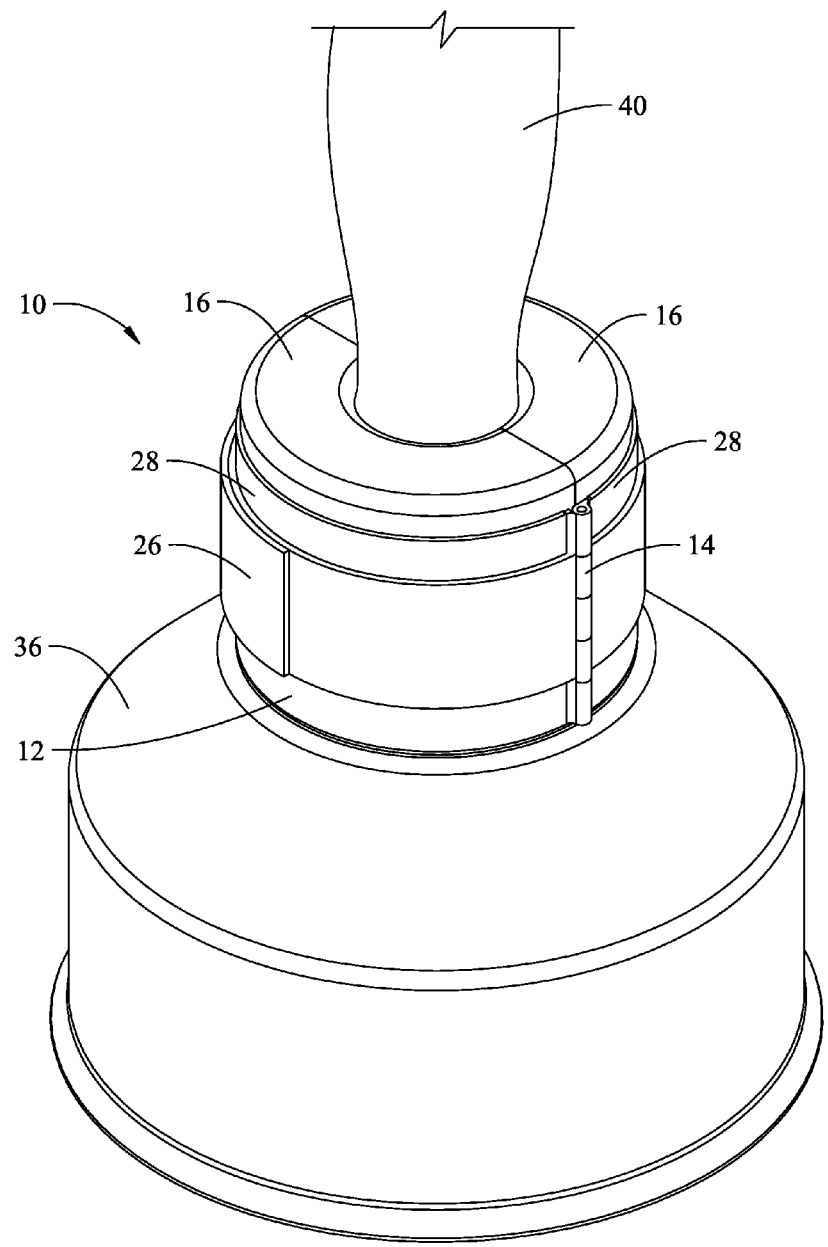
FIG. 6 is a front perspective view of an alternative embodiment of a hand and wrist restorer attached with a user arm.
Figure 7:
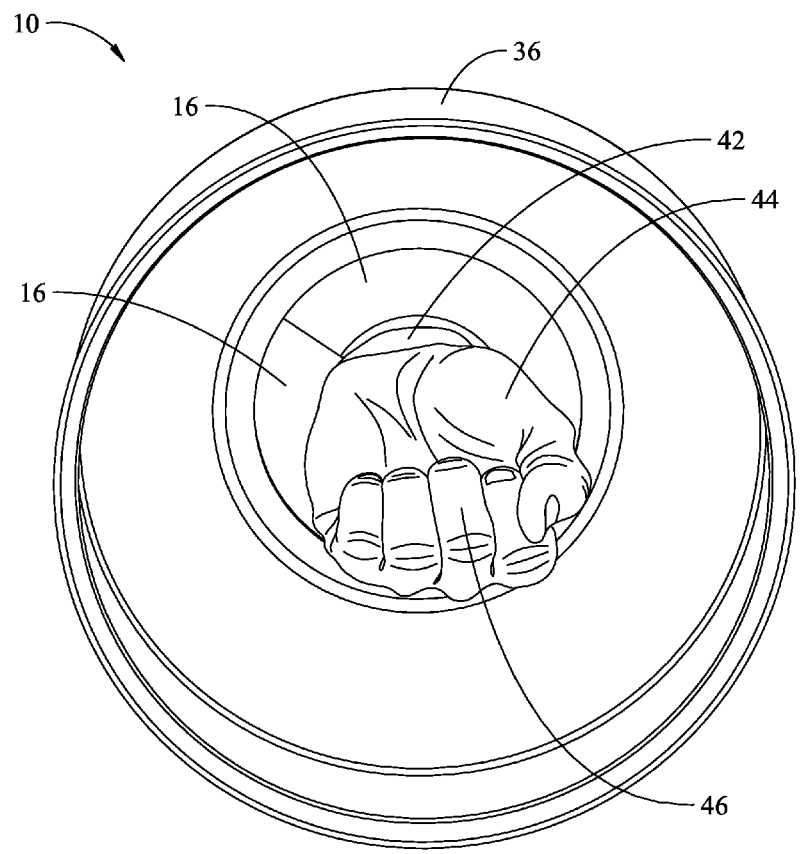
FIG. 7 is a bottom perspective view of an alternative embodiment of a hand and wrist restorer attached with a user arm and showing a user first slightly rotated.
Figure 8:
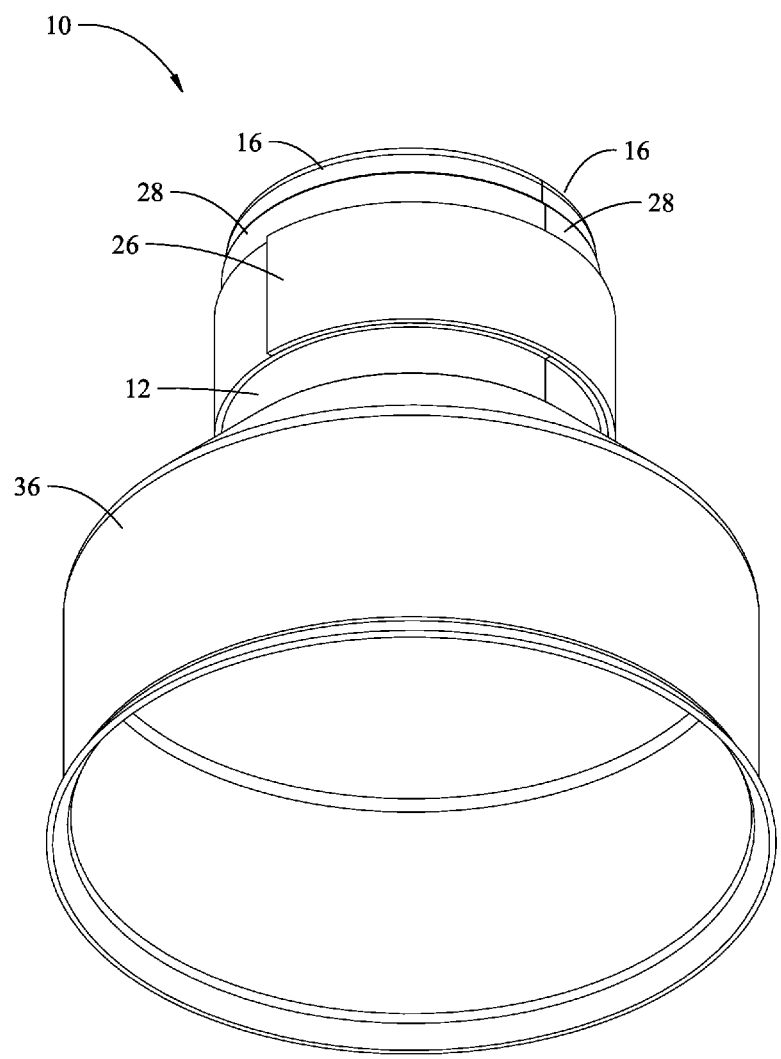
FIG. 8 is a front bottom perspective view of an alternative embodiment of a hand and wrist restorer.
Figure 9:
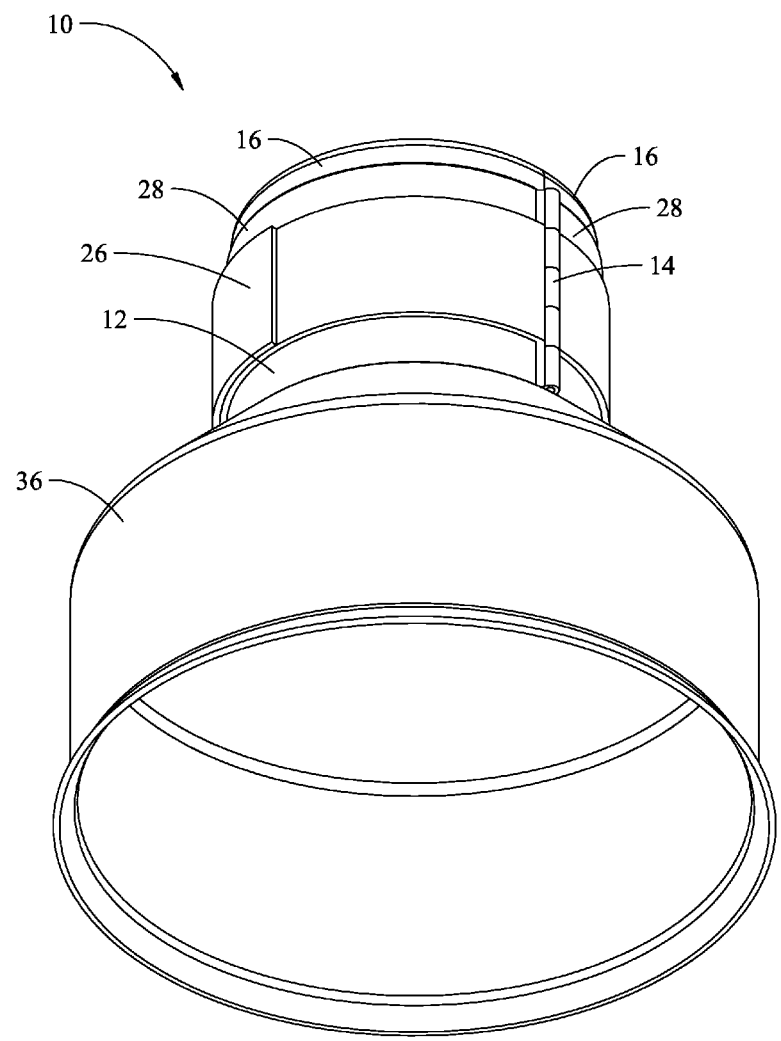
FIG. 9 is a rear bottom perspective view of an alternative embodiment of a hand and wrist restorer.
Figure 10:
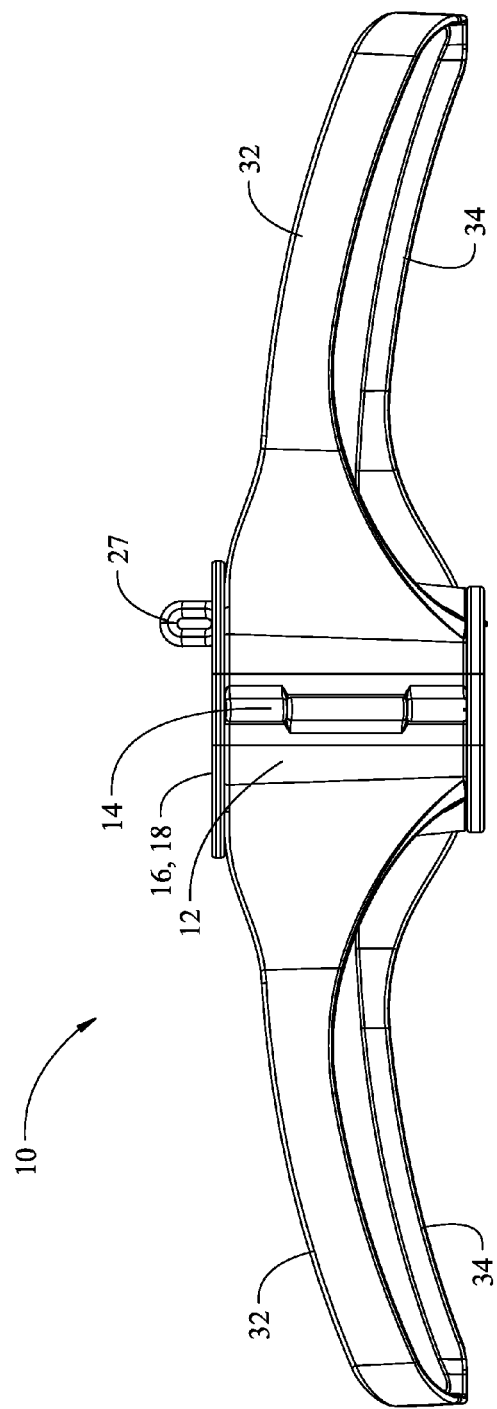
FIG. 10 is a rear plan view of a preferred embodiment of a hand and wrist restorer.
Figure 11:
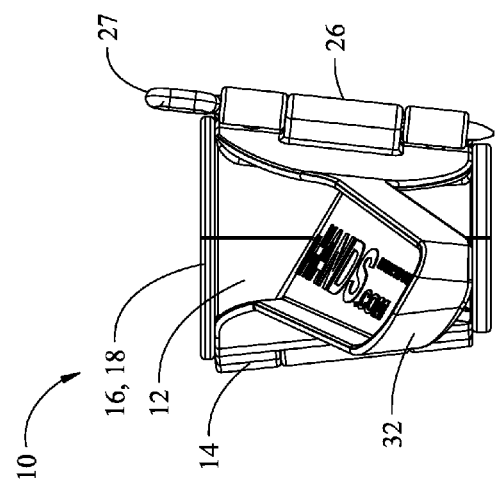
FIG. 11 is a left plan view of a preferred embodiment of a hand and wrist restorer.
Figure 12:
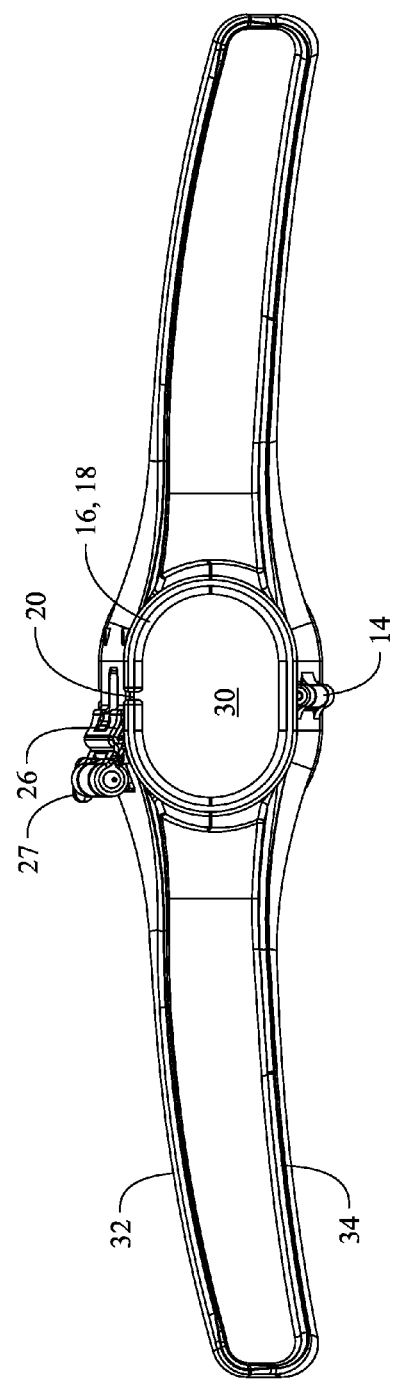
FIG. 12 is a bottom plan view of a preferred embodiment of a hand and wrist restorer.
Figure 13:
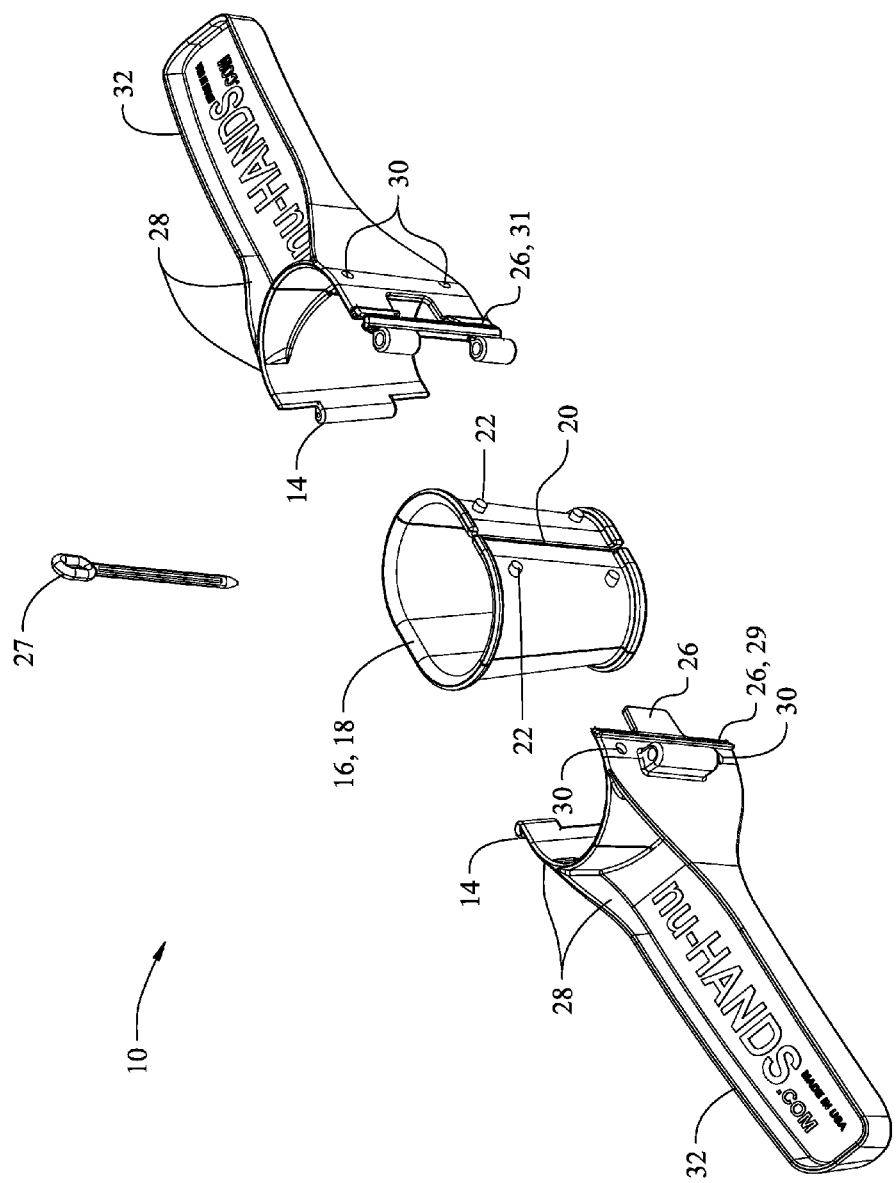
FIG. 13 is an exploded view of a preferred embodiment of a hand and wrist restorer.
Figure 14:
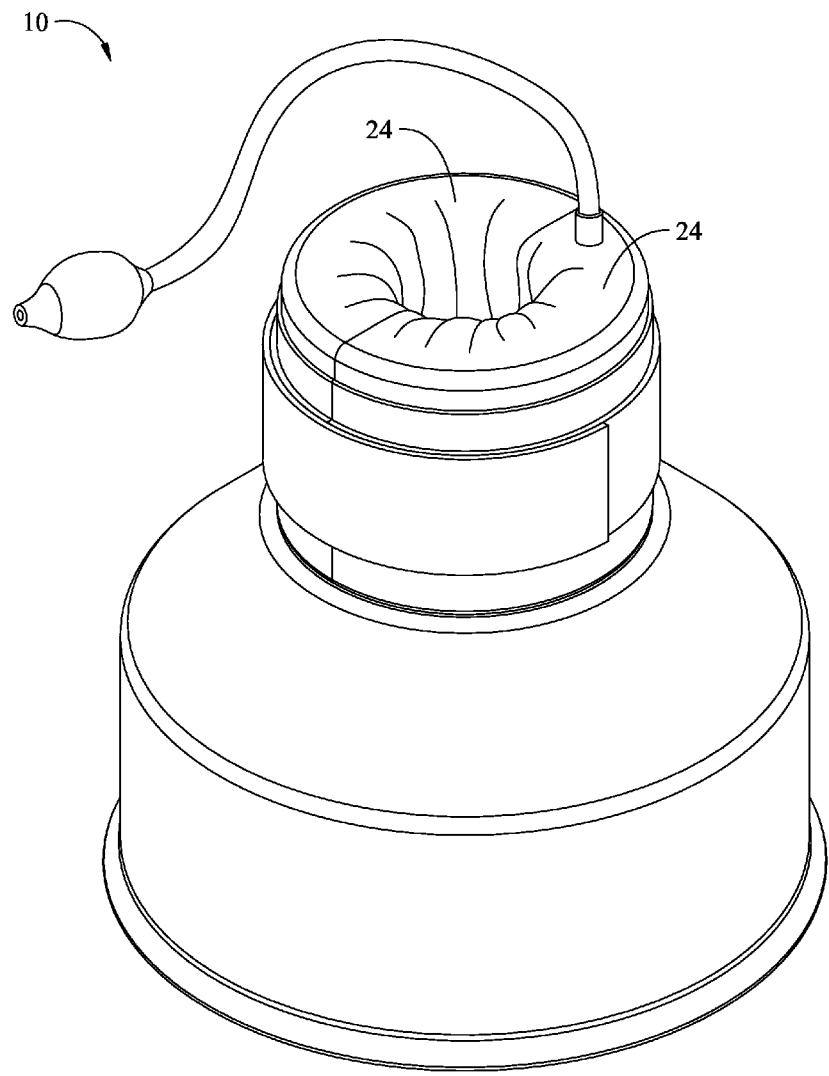
FIG. 14 is a top front perspective view of a second alternative embodiment of a hand and wrist restorer showing the pneumatic or hydraulic bladder and the two halves of a hinged portion of the cuff.
Figure 15:
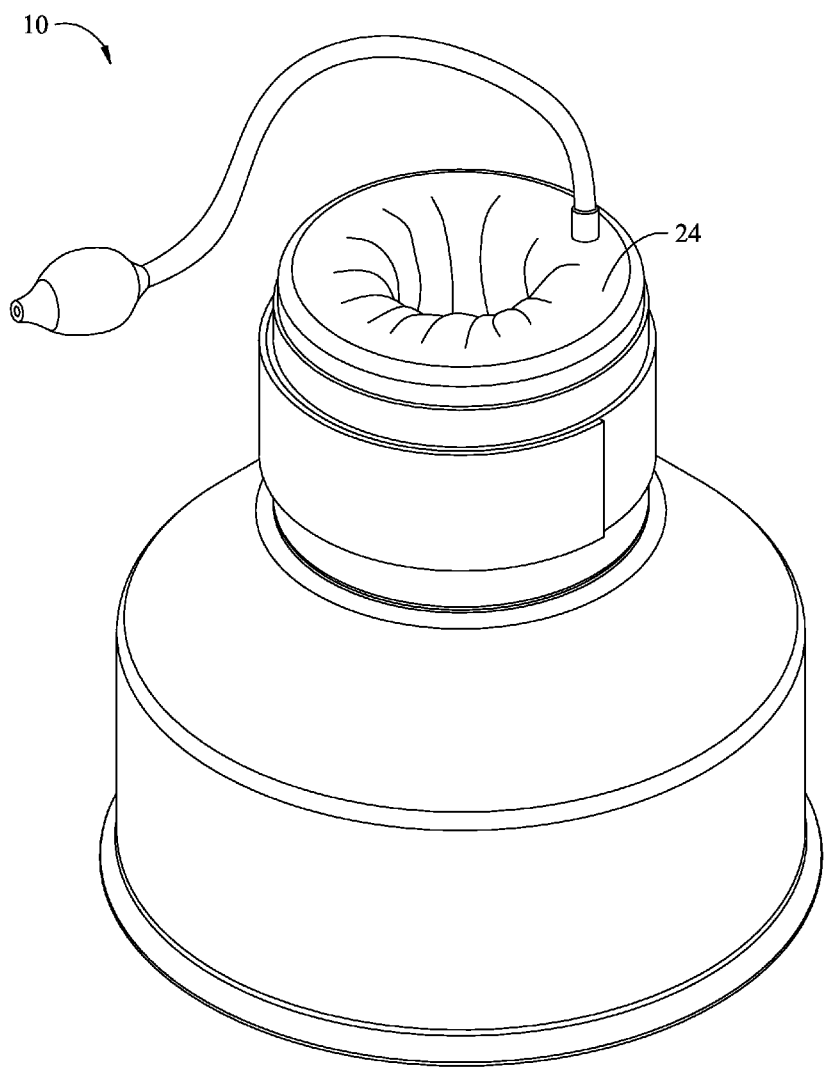
FIG. 15 is a top front perspective view of a second alternative embodiment of a hand and wrist restorer showing the pneumatic or hydraulic bladder and a closed single piece cuff.
Figure 16:
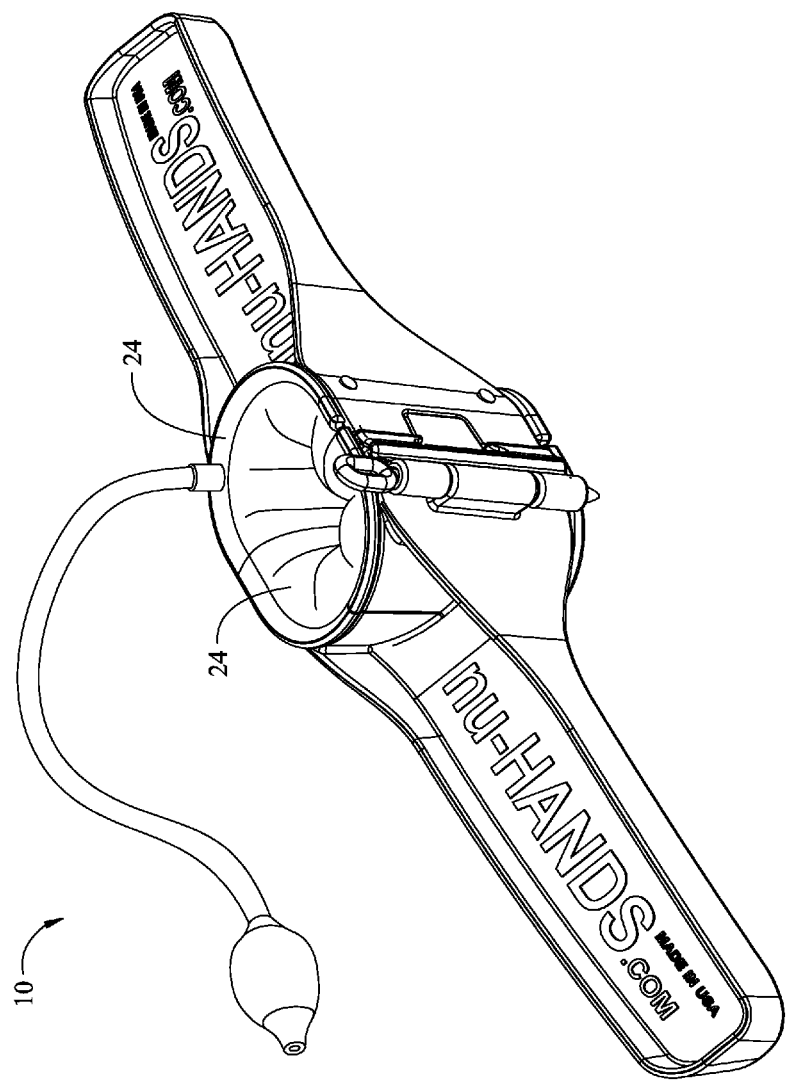
FIG. 16 is a top front perspective view of a third alternative embodiment of a hand and wrist restorer showing the pneumatic or hydraulic bladder and the two halves of a hinged portion of the cuff.
Figure 17:
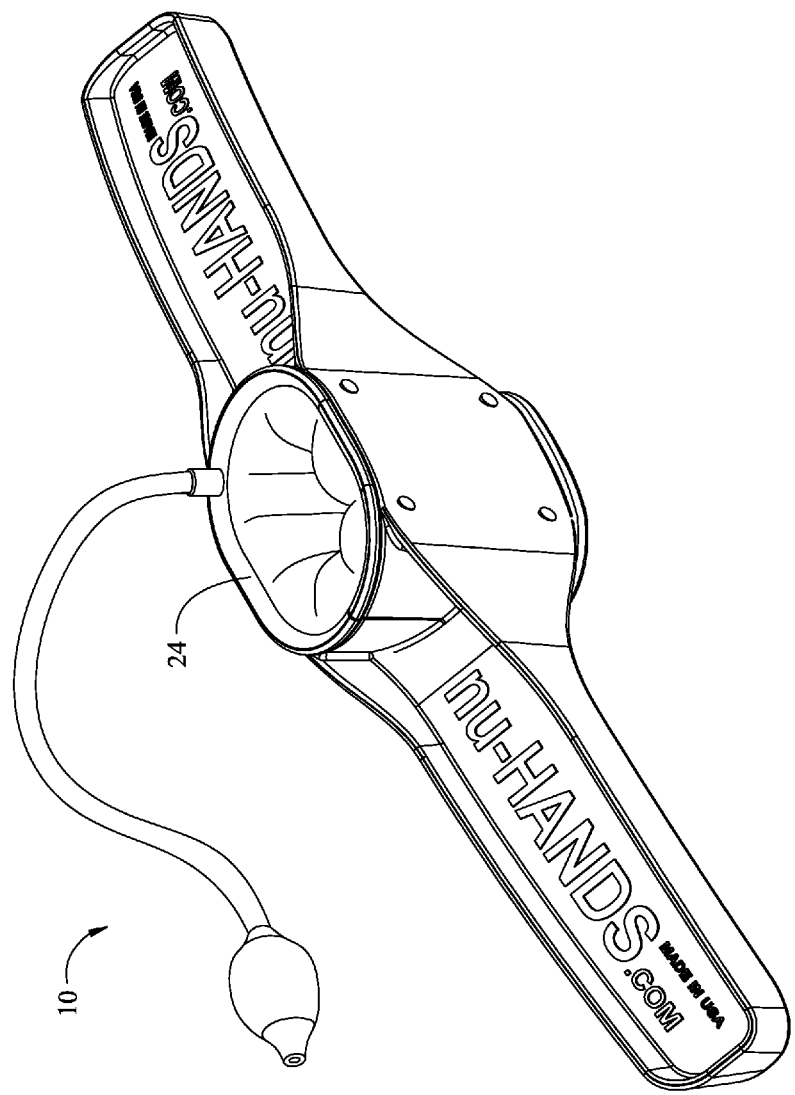
FIG. 17 is a top front perspective view of a third alternative embodiment of a hand and wrist restorer showing the pneumatic or hydraulic bladder and a closed single piece cuff.

The preferred embodiment of the present art hand and wrist restorer apparatus 10 as seen in FIGS. 1, 2, and 10-13 comprises a cuff 12 and one or more (preferably two) winged supports 32 attached with said cuff 12, said cuff 12 having a proximal 15 and distal portion 17. Preferably said winged supports 32 extend at least partially laterally from said cuff 12 and have an at least partially arcuate shape 34. The cuff 12 has an at least partially cylindrical form, i.e. having a passage 19 shaped to closely fit with the forearm or wrist of a user, and is preferably manufactured of a rigid material such as a molded or formed plastic but may be manufactured from a plurality of materials including but not limited to metals and alloys thereof, woods, ceramics, or composites. For enablement purposes only, the cuff 12 is approximately four inches in outside diameter, three inches in inside diameter, and four inches in length. The first alternative embodiment as seen in FIGS. 3-9 shares the essence of the cuff 12 of the preferred embodiment with a partial conical form 36 utilized in lieu of the winged supports 32. The second alternative embodiment as seen in FIGS. 14-15 and third alternative embodiment as seen in FIGS. 16-17 utilizes a pneumatic or hydraulic bladder 24 within the cuff 12. Said bladder 24 is shown with a mechanical bulb for pressurization but may further comprise an electrical or electronic pumping mechanism without departing from the spirit and scope of the present art. The embodiments with said bladder 24 may include said hinged portion 14 or may forego use of said hinged portion 14 and form said cuff 12 as a single or closed element through which a user's limb is placed.

For the preferred embodiment, the cuff 12 has a hinged portion 14, an inner liner 16 or lining, and a buckle or retainer 26 to maintain the cuff 12 in a closed form. The hinged portion 14 preferably is substantially parallel with the axis of the cylindrical form and allows the cylindrical form to open into two halves 28 for placement of the patients limb or forearm 40. The hinged portion 14 may comprise a traditional barrel hinge form or a plurality of other forms including but not limited to continuous or piano hinges, butt hinges, strap hinges, or a continuously molded living hinge.

The inner liner 16 or lining is preferably of a tacky rubberized material that allows a substantial grip with the limb in wet or dry conditions and forms a central passage 19 or bore for limb placement. This includes materials of a natural or synthetic rubber material, vulcanized rubber, polyurethane open or closed cell foam, or a plurality of natural or synthetic materials which provide a slight cushioning and frictional grip with the limb. Preferably the inner liner 16 or lining is mechanically or adhesively attached with the inside circumference of the cuff 12 and is separated at the opening between the two halves 28 substantially opposite the hinged portion 14. For the preferred embodiment, the inner liner represents a single molded piece 18 with a lengthwise slit 20 or openings which may open and close with the two halves 28 of the cuff 12. Said inner liner 16 preferably has one or more extensions or protrusions 22 which mate with recesses or holes 30 within the cuff 12 for retention purposes.

Further alternative embodiments utilize a pneumatic or hydraulic bladder 24 in place of said inner liner 16, with or without the hinged portion 14. The pneumatic or hydraulic bladder 24 functions and operates similar to a blood pressure cuff. The pressure placed via said cuff 12 around the forearm 40 or wrist 42 areas provides a firm grip upon the skin and fascia when placed within the central passage 19. A pump valve and release valve are provided to pressurize and vent said bladder 24 respectively. Preferably said valves are located upon the winged support 32 or the conical form 36 but may be located at a plurality of user accessible locations. Said bladder 24 may take a plurality of forms including, but not limited to, integrally mounted bladders mounted within a recess within said cuff 12, separately inserted bladders which are removable, and/or bladders which simply fit and are attached within the central passage 19 of said cuff 12.

The buckle or retainer 26 is mounted with one of the halves 28 of the cylinder or cuff 12 and is retained by the other half 28 via a retainer 26 when the two halves 28 are closed to form the somewhat cylindrical shape. The buckle or retainer 26 holds the cylindrical form of the cuff 12 onto the limb with the required force during use of the apparatus 10. The buckle or retainer 26 may take a plurality of forms including but not limited to traditional buckles having a frame, prong, and bar, clasps, or hook and loop fasteners (i.e. Velcro®). For the preferred embodiment, the retainer 26 comprises a ridge member 29 and a hook or edge portion 31, substantially from the proximal portion 15 to the distal portion 17. The two members/portions 29, 31 mate or disconnect via a flexing of the retainer 26 body during closing and opening. That is, the hook or edge portion 31 fits over and latches with the ridge member 29. For the preferred embodiment a retainer pin 27, also substantially from the proximal portion 15 to the distal portion 17, is utilized to further secure the retainer 26 when the cuff 12 is in a closed position.

For the preferred embodiment, said winged supports 32 have a shape which allows a patient to support the apparatus upon his or her thighs during use. That is, the user must be able to exert a forward or distal force and a lateral or rotational movement with a portion of the limb extending from the apparatus 10 and upon which the apparatus 10 is mounted. This requires that the apparatus 10 be supported when utilized. The winged supports 32 may also be utilized with a counter top, wall, floor or other surface in order to provide said support. For enablement purposes only, the preferred embodiment has winged supports 32 which are approximately one inch in width and six inches in length with a thickness of approximately ½ inch. Provided the winged supports 32 are capable of providing the aforesaid support, said supports 32 may take a plurality of forms including but not limited to flat, curved, arcuate, or block forms.

An alternative embodiment attaches a strap and/or handle with the cuff 12 and allows a user to hold the strap or handle with a single hand while imparting the distal or lateral forces to a particular limb portion. The handle or strap may be secured to the cuff 12 or to the winged supports 32 or to a combination of both.

A further alternative embodiment utilizes a distal cone, conical, semi-conical, partial conical, or frustum shaped form 36 in place of said winged supports 32. The alternative conical form 36 attaches with the cuff 12 and allows a patient or user to easily apply the forward force onto a surface such as a counter top, wall, or floor. The alternative conical form 36 is attached with the cuff 12 whereby the cuff 12 may be opened and closed as with other embodiments.

In operation, the patient or user first places a portion of a limb requiring treatment (usually the forearm 40 or possibly the wrist 42 area) into the open cuff 12 and closes the cuff 12. (i.e. places the limb through the central passage 19) The cuff 12 is compressed tightly around the limb and the buckle or retainer 26 is secured with the retainers 26 on the cuff 12 or the pneumatic or hydraulic bladder 24 is inflated or pressurized. This assures a firm grasp of the limb and the underlying fascia, scar, and muscle tissue. The patient or user then places the winged supports 32 onto the thighs, against a surface, or in the case of the partially conical form 36 (also known as a support) against a surface such as a table, wall, counter top, or floor and applies a distal force. If the strap and/or handle is utilized, the user will hold the handle or strap with a hand prior to therapy.

For use with the arm, therapy thereafter begins with the user preferably forming a fist-like form with the hand 44 (i.e. distal portion of the user's limb) on the arm upon which the apparatus 10 is mounted in order to maximize the fascia stretch, especially at the back of the hand 44 and knuckle areas. The patient or user then rotates the wrist 42 (either clockwise or counterclockwise). The patient or user holds the first at a particular location which feels the most stretch until the stretch feeling dissipates. Typically the holding time is on the order of two minutes but may be longer or shorter depending upon the user preference and severity of the injury or ailment. Upon release, the hand 44 will have a red like appearance and a tingling feel which is a normal condition. When the apparatus 10 is removed, the patient or user will have a looser feeling or more nimble hand 44, wrist 42, and fingers 46. The fascia and scar tissue fibers will be stretched and not constrict the muscle movement as was experienced prior to operation of the apparatus.

Although contemplated and described for use with an arm or forearm 40, the art of the present invention may also be utilized with the legs. That is, the user can mount the cuff 12 around the lower leg, thereby grasping the fascia tissue, and thereafter rotate the foot to obtain the aforesaid benefits for the lower leg.

Although described for enablement purposes, the lengths, widths, and other dimensional attributes may depart significantly from those specified. The shape, size, location, component numbers and mounting methods utilized for the components described may take a plurality of forms as recognized within pertinent arts without departing from the scope and spirit of the present invention.

Having described the invention in detail, those skilled in the art will appreciate that modifications may be made to the invention and its method of use without departing from the spirit herein identified. Therefore, it is not intended that the scope of the invention be limited to the specific embodiments illustrated and described. Rather, it is intended that the scope of this invention be determined by the appended claims and their equivalents. No claim is made to any part of the human body; any reference thereto within the appended claims is provided for method of use purposes only or to more fully describe the present art apparatus and method of use.

What is claimed is:

1. A method of restoring functions of a user's limb via contacting of the user's limb and grasping an underlying fascia tissue and stretching of the underlying fascia tissue between the grasping portion and a distal portion of the user's limb, the steps comprising:

forming a cuff having a proximal and distal portion and having a liner and a passage of a size sufficient to allow insertion of the user's limb; and forming a gripping surface with said liner which is capable of contacting and frictionally holding with the user's limb; and forming one or more supports extending and attached with said cuff; and inserting the user's limb through said cuff and liner; and compressing said cuff around the user's limb and gripping a portion of a skin of the limb with the limb distal portion extending from said cuff and thereby grasping the underlying fascia tissue; and placing one or more of said supports upon a surface in a manner which will allow any distal portion of the user's limb extending from said cuff to rotate; and applying a distal force to said cuff via said cuff gripping the skin and fascia with the user's limb; and rotating any distal portion of the user's limb extending through said cuff and liner and stretching the underlying fascia tissue.

2. The method of restoring functions of a user's limb as set forth in claim 1, the steps further comprising:

forming said cuff from two halves; and placing a hinged portion between said two halves; and placing a retainer between said two halves whereby said cuff may open and close upon said hinge and be retained via said retainer.

3. The method of restoring functions of a user's limb as set forth in claim 2, the steps further comprising:

forming said inner liner from a single molded piece of rubber like rubberized material capable of providing a slight cushioning and a frictional grip; and forming a lengthwise slit within said inner liner whereby said inner liner may open and close with said cuff.

4. The method of restoring functions of a user's limb as set forth in claim 3, the steps further comprising:

forming said one or more supports into winged supports extending at least partially laterally from said cuff; and utilizing one or more of a user's thighs as said surface.

5. The method of restoring functions of a user's limb as set forth in claim 4, the steps further comprising:

forming one or more of said supports into an at least partially arcuate shape.

6. The method of restoring functions of a user's limb via contacting of the user's limb and grasping an underlying fascia tissue and stretching of the underlying fascia tissue between the grasping portion and a distal portion of the user's limb, the steps comprising:

forming a cuff having a proximal and distal portion and having a liner and a passage of a size sufficient to allow insertion of the user's limb; and forming a gripping surface with said liner which is capable of contacting and frictionally holding with the user's limb; and forming one or more supports with said cuff; and inserting the user's limb through said cuff and liner; and compressing said cuff around the user's limb and gripping a skin of the limb with the limb distal portion extending from said cuff and thereby grasping the underlying fascia tissue; and placing one or more of said supports upon a surface in a manner which will allow any portion of the user's limb extending through said cuff to rotate; and applying a distal force to said cuff via said cuff gripping the skin and fascia with the user's limb; and rotating any distal portion of the user's limb extending through said cuff and liner and stretching the underlying fascia tissue; and forming said one or more supports into winged supports extending at least partially laterally from said cuff; and utilizing one or more of a user's thighs as said surface.

7. The method of restoring functions of a user's limb set forth in claim 6, the steps further comprising:

forming one or more of said supports into an at least partially arcuate shape.

\* \* \* \* \*